(12) United States Patent
Cheng et al.

(10) Patent No.: US 11,365,267 B2
(45) Date of Patent: Jun. 21, 2022

(54) FLUORINE-CONTAINING ALTERNATING COPOLYMER MACROMONOMER AND SYNTHESIS METHOD THEREOF

(71) Applicant: SOOCHOW UNIVERSITY, Suzhou (CN)

(72) Inventors: Zhenping Cheng, Suzhou (CN); Jiannan Cheng, Suzhou (CN); Jinying Wang, Suzhou (CN); Kai Tu, Suzhou (CN); Xiulin Zhu, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 241 days.

(21) Appl. No.: 16/961,907

(22) PCT Filed: Jun. 14, 2019

(86) PCT No.: PCT/CN2019/091183
§ 371 (c)(1),
(2) Date: Jul. 13, 2020

(87) PCT Pub. No.: WO2020/243986
PCT Pub. Date: Dec. 10, 2020

(65) Prior Publication Data
US 2021/0403612 A1 Dec. 30, 2021

(30) Foreign Application Priority Data
Jun. 4, 2019 (CN) .......................... 201910482403.7

(51) Int. Cl.
*C08F 2/06* (2006.01)
*C08F 2/44* (2006.01)
(Continued)

(52) U.S. Cl.
CPC .................. *C08F 2/06* (2013.01); *C08F 2/44* (2013.01); *C08F 4/04* (2013.01); *C08F 4/34* (2013.01); *C08F 220/18* (2013.01); *C08F 259/08* (2013.01)

(58) Field of Classification Search
CPC ........ C08F 14/185; C08F 14/18; C08F 20/38; C08F 20/22
See application file for complete search history.

(56) References Cited

U.S. PATENT DOCUMENTS 3,655,732 A * 4/1972 Rondestvedt ........... C08F 20/34
560/222
3,686,283 A * 8/1972 Gresham ............... C07C 323/00
525/200
(Continued)

FOREIGN PATENT DOCUMENTS

| CN | 104530309 A | 4/2015 |
| CN | 105482013 A | 4/2016 |
| CN | 107619466 A | 1/2018 |

OTHER PUBLICATIONS

Xu, RSC Advances, 2017, 7, p. 17988-17996 (Year: 2017).*

*Primary Examiner* — Robert C Boyle
(74) *Attorney, Agent, or Firm* — SZDC Law P.C.

(57) ABSTRACT

The present invention relates to a fluorine-containing alternating copolymer macromonomer and a synthesis method thereof. The synthesis method comprises steps of: subjecting a fluorine-containing alternating copolymer to a reduction reaction at 60-100° C. in an organic solvent in the presence of a reducing agent and a first catalyst to obtain a reduction product; in the presence of a second catalyst, reacting the reduction product with a mercapto-monohydric alcohol in an organic solvent at 60-100° C., to obtain a hydroxyl-terminated fluorine-containing alternating copolymer; and in the presence of a third catalyst, reacting the hydroxyl-termi- (Continued)

nated fluorine-containing alternating copolymer with an acrylic monomer or acryloyl chloride monomer at 0-30° C., to obtain the fluorine-containing alternating copolymer macromonomer. In the present invention, a fluorine-containing alternating copolymer macromonomer is initially synthesized from a fluorine-containing alternating copolymer through polymer modification.

10 Claims, 7 Drawing Sheets

(51) Int. Cl.
*C08F 4/04* (2006.01)
*C08F 4/34* (2006.01)
*C08F 220/18* (2006.01)
*C08F 259/08* (2006.01)

(56) References Cited

U.S. PATENT DOCUMENTS

| | | | | |
|---|---|---|---|---|
| 3,884,879 A | * | 5/1975 | Kleiner | D06M 15/277 |
| | | | | 568/45 |
| 2004/0198702 A1 | * | 10/2004 | Petrova | C07C 323/12 |
| | | | | 514/142 |

* cited by examiner

FLUORINE-CONTAINING ALTERNATING COPOLYMER MACROMONOMER AND SYNTHESIS METHOD THEREOF

This application is the National Stage Application of PCT/CN2019/091183, filed on Jun. 14, 2019, which claims priority to Chinese Patent Application No. 201910482403.7, filed on Jun. 4, 2019, which is incorporated by reference for all purposes as if fully set forth herein.

FIELD OF THE INVENTION

The present invention relates to the technical field of organic synthesis, and more particularly to a fluorine-containing alternating copolymer macromonomer and a synthesis method thereof.

DESCRIPTION OF THE RELATED ART

Macromonomers are also referred to as macromers, which have a polymerizable end group compared with a common linear polymer. A macromer can be copolymerized with a common monomer to obtain a graft copolymer. The side chain of such a graft copolymer has uniform molecular weight and even length. The branching density of the branched copolymer can be controlled by changing the amount of macromer added. Macromers can also be used to prepare block copolymers or branched polymers with high graft density. The copolymers synthesized by macromers have regular structure, so the importance of the method for synthesizing regular copolymers with macromonomers is self-evident.

At present, there are many methods for preparing macromonomers. For example, (1) living polymerization initiator method: a C=C-containing alcohol is allowed to react with trifluoromethanesulfonic acid by Dubreuil et al. to form an ester, and then cationic polymerization of tetrahydrofuran (THF) is initiated, to produce a macromonomer. The ester produced by quantitative reaction of difluoromethanesulfonic acid and allyl alcohol allows the cationic polymerization of THF to be well controlled, and finally an allyl type polytetrahydrofuran macromonomer is produced (Dubrenil, M. F.; Goethals, E. *J. Macromol. Chem. Phys.* 1999, 198, 3077). Miyashita et al. used β-hydroxyethyl methacrylate as a starting agent and HCl/SnCl$_4$/n-Bu$_4$NCl as an initiator, and then initiated the cationic polymerization of styrene and p-methoxystyrene to prepare a methacryloyl-type macromonomer with narrow molecular weight distribution and a functionality that is very close to 1 (Miyashita, K.; Kamigaito, K.; Sawamoto, M. *Macromolecules* 1994, 27, 1093). (2) Living polymerization terminator method: 3-methylacryloyloxypropyl-dimethylchlorosilane is used by Mera et al. to terminate the anionic polymerization of cyclotrisiloxane initiated by sec-butyllithium (s-BuLi) to produce a methacryloyl-type macromonomer of polydimethylsiloxane (PDMS) and fluorine-containing polysiloxane (Mera, A. E.; Goodwin, M.; Pike, K. J. *Polymer* 1999, 40, 419). p-(2-chloroethyl)-α-methylstyrene is used by Se et al. to terminate the anionic polymerization of poly-α-methylstyrene, where the molecular weight of the macromonomer produced by the reaction is between 2000 and 7100, and the polydispersity index is 1.09 to 1.12; and the termination efficiency is not less than 0.98 (Se, K. Suzuki, M.; Mastuo, T. *Kobunshi Robunshu* 1992, 49, 817). (3) Chain transfer method of free radical polymerization: α-iodovinyl acetate is used by Teodorescu as a chain transfer agent, and finally a vinyl acetate-type polystyrene macromonomer is produced (Teodorescu, M. *Eur. Polym. J.* 2001, 37, 1417). Nair et al. used 5-tert-butylthio-1,3-pentadiene as a chain transfer agent for the free radical polymerization of methyl methacrylate and styrene to prepare a diene-type macromonomer (Nair, C. P. R.; Chaumont, P.; Charmot, D. *J. Polym. Sci. Part A: Polym. Chem.* 1995, 33, 2773). As mentioned above, although there are many methods for synthesizing macromonomers, there have been no reports concerning fluorine-containing alternating copolymer macromers so far.

Compared with a linear polymer with the same molecular weight, an amphiphilic comb-like polymer can have a denser structure and smaller size in solution, and the hydrophobic and hydrophilic moieties of the polymer are incompatible with each other, so microphase separation tends to occur. In a selective solvent, the moieties in the molecules that are equally hydrophilic or lipophilic tend to aggregate with each other to form micelles. Therefore, the self-assembled structure of amphiphilic comb-like polymers has promising prospects in the fields of biology, medicine and nanotechnology.

Among the comb-like polymers, the comb-like polymer with fluorine-containing side chains allows more stable self-assembly due to the hydrophobicity and oleophobicity of the fluorine-containing chain ends. Therefore, the self-assembly of the comb-like polymer with fluorine-containing side chains is of great research value. However, the fluoropolymer side chains are all constructed with general fluorine-containing (meth)acrylate at present. The available monomer structure is simple, so the structure of resulting polymer is not sufficiently adjustable.

SUMMARY OF THE INVENTION

To solve the above technical problems, an object of the present invention is to provide a fluorine-containing alternating copolymer macromonomer and a synthesis method thereof. In the present invention, a fluorine-containing alternating copolymer macromonomer is initially synthesized from a fluorine-containing alternating copolymer through the subsequent polymer modification.

A first object of the present invention is to provide a method for synthesizing a fluorine-containing alternating copolymer macromonomer, which comprises the following steps:

(1) subjecting a fluorine-containing alternating copolymer of Formula (1) to a reduction reaction at a reaction temperature of 60-100° C. in an organic solvent in the presence of a reducing agent and a first catalyst, to obtain a reduction product of Formula (2) after the reaction is completed:

where a=4-8, b=2-6, and n=1-30;

(2) in the presence of a second catalyst, reacting the reduction product with a mercapto-monohydric alcohol of Formula (3) in an organic solvent at 60-100° C., to obtain a hydroxyl-terminated fluorine-containing alternating copolymer of Formula (4) after the reaction is completed:

where c=1-10, a=4-8, b=2-6, and n=1-30; and (3) in the presence of a third catalyst, reacting the hydroxyl-terminated fluorine-containing alternating copolymer with an acrylic monomer or acryloyl chloride monomer at 0-30° C., to obtain the fluorine-containing alternating copolymer macromonomer after the reaction is completed.

In an embodiment, in Step (1), the molar ratio of the fluorine-containing alternating copolymer and the reducing agent is 1:2-100, and the reducing agent is tributyltin hydride ($Bu_3HSn$). Preferably, the molar ratio of the fluorine-containing alternating copolymer and the reducing agent is 1:5-50, and more preferably 1:10.

In an embodiment, in Step (1), the molar ratio of the fluorine-containing alternating copolymer and the first catalyst is 1: 2-300, and the first catalyst is azobisisobutyronitrile (AIBN), or dibenzoyl peroxide (BPO). Preferably, the molar ratio of the fluorine-containing alternating copolymer and the first catalyst is 1:10-150, and more preferably 1:30.

In a preferred embodiment, in Step (1), the organic solvent is toluene, chloroform, or N,N-dimethylformamide (DMF).

In Step (1), the fluorine-containing alternating copolymer is obtained through Step Transfer-Addition & Radical Termination (START) polymerization, and the copolymer has a terminal reactive functional group (C=C). The preparation method is as described in CN107619466 A. Since the side chain of the fluorine-containing alternating copolymer of Formula (1) contains a weak C—I bond, it cannot undergo free radical addition with the mercapto-monohydric alcohol. Therefore, the C—I bond on the side chain is reduced by a reducing agent.

In an embodiment, in Step (2), the second catalyst is 1,1'-azo (cyanocyclohexane) (ACBN), or azobisisobutyronitrile (AIBN); and the molar ratio of the reduction product and the second catalyst is 1:3-6.

In an embodiment, in Step (2), the molar ratio of the reduction product to the mercapto-monoalcohol is 1:10-100.

In an embodiment, in Step (2), the organic solvent is selected from the group consisting of toluene, chloroform, N,N-dimethylformamide (DMF), dimethyl sulfoxide (DMSO) and any combination thereof.

In an embodiment, in Step (3), the third catalyst is triethylamine, and pyridine; and the molar ratio of the hydroxyl-terminated fluorine-containing alternating copolymer to the third catalyst is 1:1.5-3.

In an embodiment, in Step (3), the acrylic monomer is methacrylic acid, or acrylic acid.

In an embodiment, in Step (3), the acryloyl chloride monomer is methacryloyl chloride, or acryloyl chloride.

In an embodiment, in Step (3), the molar ratio of the hydroxyl-terminated fluorine-containing alternating copolymer to the acrylic monomer or acryloyl chloride monomer is 1:1.1-2.

In an embodiment, in Step (3), the organic solvent is chloroform or methylene chloride.

A second object of the present invention is to provide a fluorine-containing alternating copolymer macromonomer prepared by the above method, which has a chemical Formula (5).

where R=H or $CH_3$, c=1-10, a=4-8, b=2-6, and n=1-30.

The fluorine-containing alternating copolymer macromonomer has a molecular weight of 540-16500 g/mol.

In the present invention, the fluorine-containing alternating copolymer of Formula (1) is reduced and then subjected to free radical addition with a mercapto-monohydric alcohol to obtain a fluorine-containing alternating copolymer having a terminal hydroxyl group (—OH), and then the terminal hydroxyl group is reacted with an acrylic monomer or acryloyl chloride monomer to finally produce the fluorine-containing alternating copolymer macromonomer. The fluorine-containing alternating copolymer macromonomer prepared in the present invention can be subsequently polymerized into a comb-like polymer with a side chain containing fluorine. Such a polymer can be used to coat oil-soluble quantum dots or hydrophobic drugs. This polymer can be transformed into amphiphilic copolymer by means of copolymerization with a water-soluble monomer. According to specific needs, some biomolecules can be connected through —COOH on the surface of the polymer. This multi-functional nanoparticle will have broad application prospects in biomedical detection and treatment.

By virtue of the above solution, the present invention has the following advantages.

The present invention provides a novel fluorine-containing alternating copolymer macromonomer and a preparation method thereof. The copolymerization of the monomer and a water-soluble monomer can be used to prepare an amphiphilic comb-like polymer and has a good application prospect in the fields of biology, medicine and nanotechnology.

The above description is only a summary of the technical solutions of the present invention. To make the technical means of the present invention clearer and implementable in accordance with the disclosure of the specification, the preferred embodiments of the present invention will be described in detail with reference to the accompanying drawings.

DETAILED DESCRIPTION OF THE PREFERRED EMBODIMENTS

The specific embodiments of the present invention will be described in further detail with reference to the accompanying drawings and examples. The following examples are intended to illustrate the present invention, instead of limiting the scope of the present invention.

In the following examples of the present invention, 1,7-octadiene and methacryloyl chloride need to run through a neutral alumina column before use, while all other chemical reagents can be obtained commercially and used directly.

The characterization conditions of the product are as follows:

$^1$H NMR and $^{19}$F NMR: INOVA 600 MHz Nuclear Magnetic Resonance Spectrometer, solvent CDCl$_3$, and internal standard TMS;

Preparation of test samples for $^1$H NMR and $^{19}$F NMR: About 15 mg of the sample was weighed, fed to an NMR tube, and added with 0.6 mL of CDCl$_3$.

Molecular weight ($M_n$) and polydispersity index (PDI): Waters 1515 Gel Permeation chromatograph (GPC), mobile phase tetrahydrofuran (THF), and column temperature: 30° C.

Preparation of test samples for GPC: About 10 mg of the sample was weighed, dissolved in 3-4 mL of THF, filtered through a syringe filter after thorough dissolution, and added to a sample vial.

Example 1 Synthesis of Fluorine-Containing Alternating Copolymer $(AB)_n$

Dodecafluoro-1,6-diiodohexane ($C_6F_{12}I_2$), sodium ascorbate (AsAc—Na), tris(bipyridine)ruthenium dichloride (Ru(bpy)$_3$Cl$_2$), methanol (1 mL), 1,4-dioxane (3 mL), and 1,7-octadiene ($C_8H_{14}$) were sequentially added to a 5 mL ampoule in proportion, where the ratio of $[C_6F_{12}I_2]_0$:$[C_8H_{14}]_0$:$[Ru(bpy)_3Cl_2]_0$:$[AsAc—Na]_0$=1:1:0.002:0.5 (molar ratio), based on 0.5 mmol of dodecafluoro-1,6-diiodohexane. After adding a stir bar, three rounds of freezing-evacuating-introducing argon were performed, and the ampoule was flame-sealed. The ampoule was positioned under blue LED irradiation and stirred at room temperature. At this time, the solution appeared bright red. After a predetermined time of reaction, the ampoule was removed. The solution appeared dark brown. The solution was diluted with 1-2 mL of tetrahydrofuran, precipitated in a large amount of methanol in a disposable plastic cup, sealed with a plastic wrap and allowed to stand overnight in a refrigerator. Suction filtration under reduced pressure afforded a purple-black product, which was then dissolved with a small amount of tetrahydrofuran, passed through a neutral alumina column to remove metal salts, and precipitated in a large amount of methanol. The precipitate was white at this time. After standing overnight in a refrigerator, suction filtration under reduced pressure afforded a white product. The resulting white product was dried to a constant weight in a thermostatic oven at 40° C. under vacuum, and then weighed. Finally, a fluorine-containing alternating copolymer $(AB)_n$ was obtained (yield 95%). The fluorine-containing alternating copolymer $(AB)_n$ has the following chemical structure:

(1)

where a=6, b=4, and n=6-7.

Figure 1:
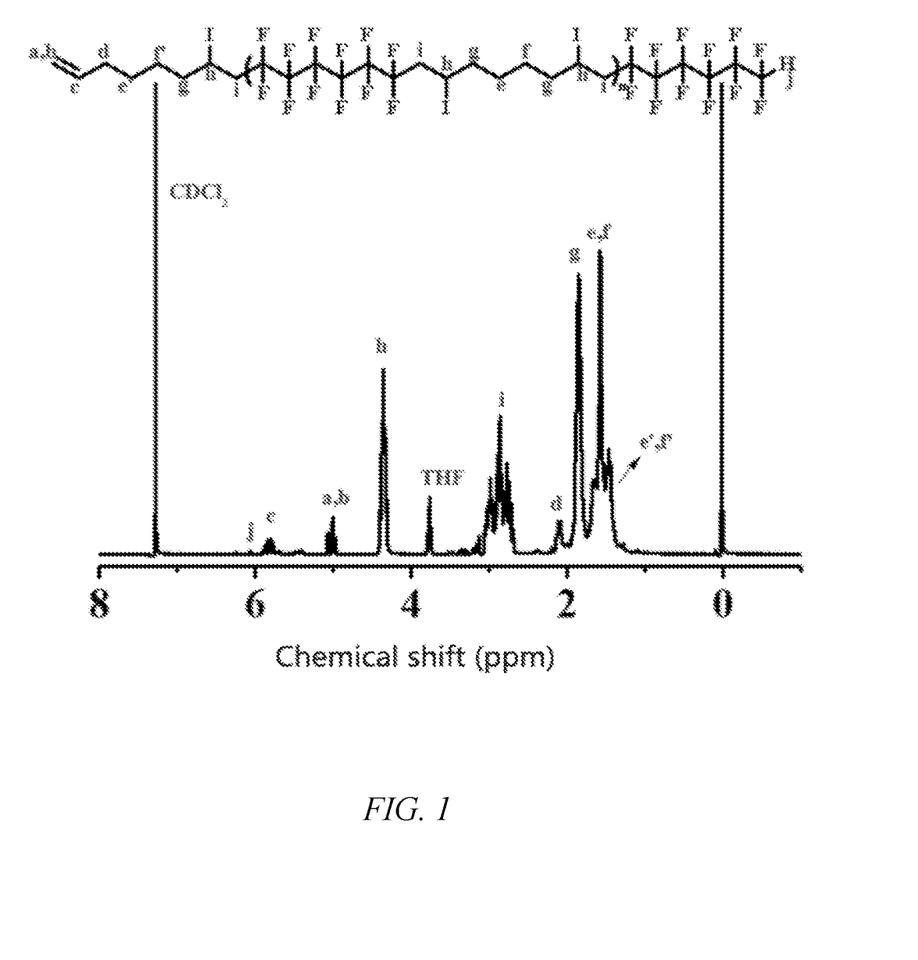
FIG. 1 shows the test results by $^1H$ NMR of a fluorine-containing alternating copolymer $(AB)_n$ prepared in Example 1 of the present invention.
Figure 2:
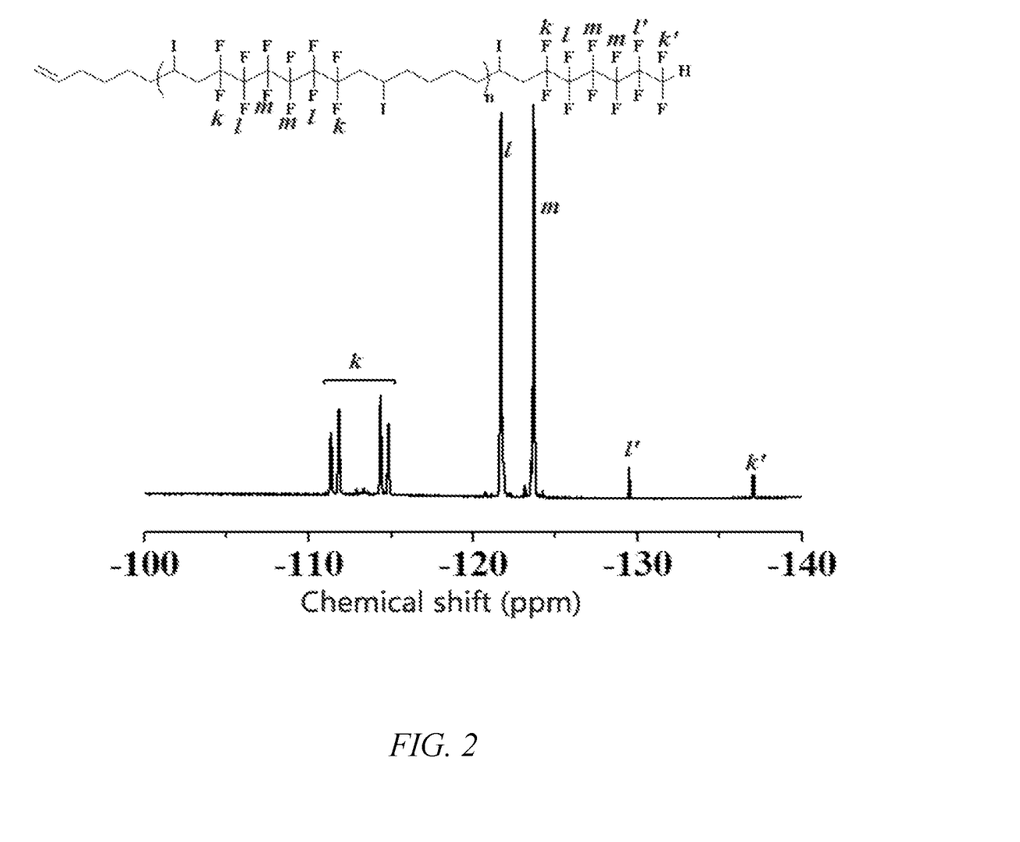
FIG. 2 shows the test results by $^{19}F$ NMR of the fluorine-containing alternating copolymer $(AB)_n$ prepared in Example 1 of the present invention.

The molecular weight ($M_n$) and polydispersity index (PDI) of the polymer were measured by gel permeation chromatography (GPC), and the structure was characterized by $^1$H NMR and $^{19}$F NMR. The results are shown in FIGS. 1-2. In FIG. 1, the peaks at different chemical shifts on the NMR spectrum can be attributed to corresponding moieties in the structural formula of the polymer. The peak at 7.26 ppm is the shift peak of deuterated chloroform (CDCl$_3$), and the peak at 3.76 ppm is the shift peak of —CH$_2$ of tetrahydrofuran (THF). In FIG. 2, the peaks at different chemical shifts on the NMR spectrum can be attributed to corresponding moieties in the structural formula. The above results indicate that the expected fluorine-containing alternating copolymer $(AB)_n$ is obtained through the above-mentioned steps.

Example 2 Reduction of $(AB)_n$

Tributyl tin hydride was used as a reducing agent and azobisisobutyronitrile (AIBN) was used as a catalyst. The resulting fluorine-containing alternating copolymer $(AB)_n$ was reduced. The reaction route and specific steps were as follows.

The fluorine-containing alternating copolymer $(AB)_n$ (1 eq.) prepared in Example 1, azobisisobutyronitrile (30 eq.), toluene (6.0 mL), and tributyl tin hydride (10 eq.) were weighed in proportion sequentially and added to a 10 mL ampoule. After adding a stir bar, three rounds of freezing-evacuating-introducing argon were performed, and the ampoule was flame-sealed. The ampoule was placed in an oil bath at 90° C., stirred, reacted for a predetermined period of time and then removed. The ampoule was opened, and the solution was diluted with 1-2 mL of tetrahydrofuran, precipitated in a large amount of methanol, sealed with a plastic wrap and allowed to stand overnight in a refrigerator. Suction filtration under reduced pressure afforded a white product. The resulting white product was dried to a constant weight in a thermostatic oven at 40° C. under vacuum, and then weighed. Finally, a reduced fluorine-containing alternating copolymer was obtained.

Figure 3:
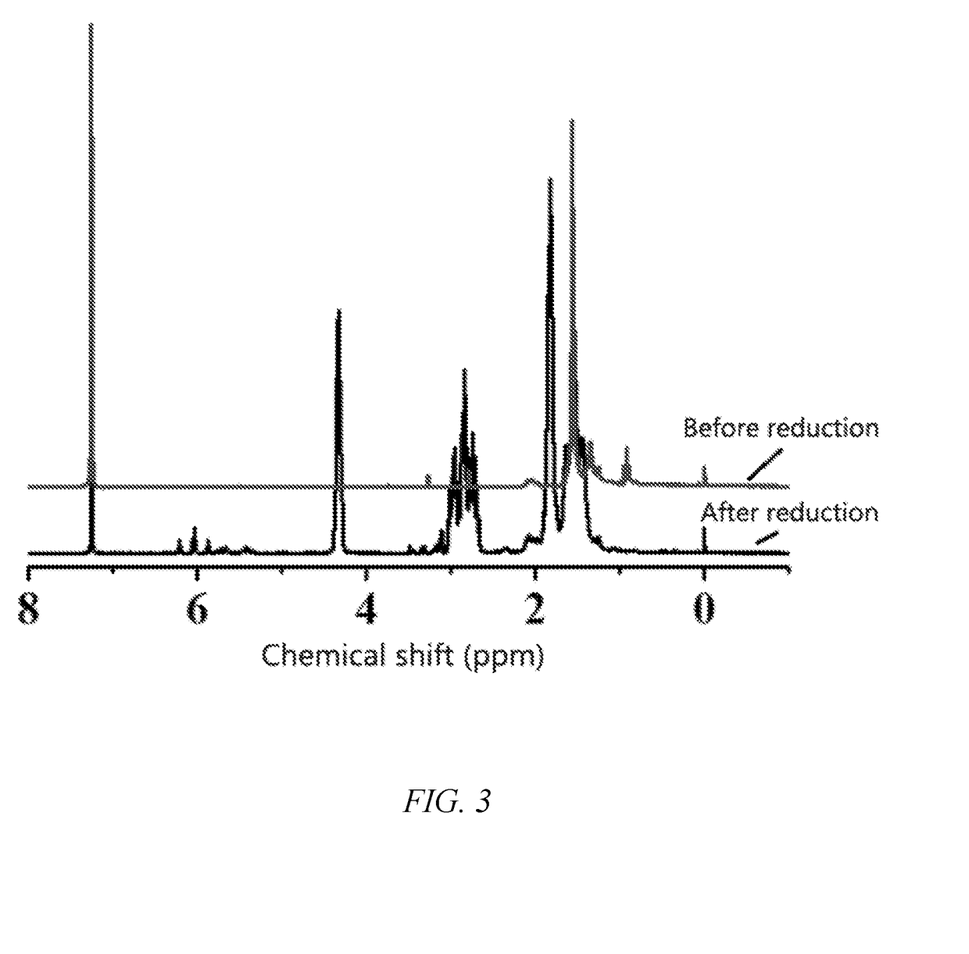
FIG. 3 shows the test results by $^1H$ NMR of the fluorine-containing alternating copolymer $(AB)_n$ before and after reduction in Example 2 of the present invention.

FIG. 3 shows the $^1$H NMR spectrum of $(AB)_n$ before and after reduction. After reduction of the C—I bond, the shift peak around the shift peak attributed to —CH$_2$CH(I)CH$_2$— (4.3 ppm) is attributed to hydrogen which is on the same carbon with iodo before reduction, and the shift peak at about 2.9 ppm is attributed to the fact that hydrogen on a carbon adjacent to the carbon to which iodo is attached before reduction disappears, and a new shift peak of —CH$_2$CH$_2$CH$_2$— is incorporated into the shift peaks at 1-2 ppm.

Figure 4:
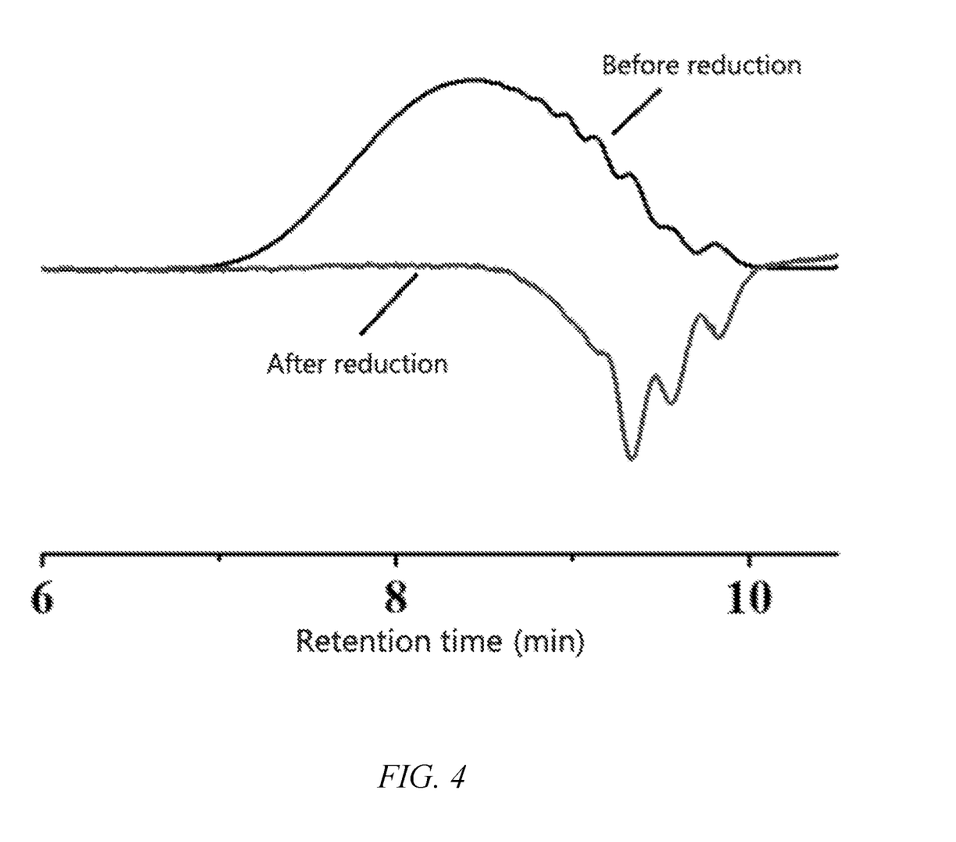
FIG. 4 shows the test results by GPC of the fluorine-containing alternating copolymer $(AB)_n$ before and after reduction in Example 2 of the present invention.

FIG. 4 shows a GPC chromatogram of $(AB)_n$ before and after reduction. It can be seen that before reduction, the molecular weight of $(AB)_n$ is 6000 g/mol, and $M_w/M_n$=1.69; and after reduction, the molecular weight of the product is 3000 g/mol, and $M_w/M_n$=1.07. After reduction, the molecular weight is negatively increased, which corresponds to the report regarding commercial fluorine-containing polyolefins (where the inverted peak is caused by that refractive index of the sample is less than that of the mobile phase). The decrease in molecular weight after reduction prevents steric hindrance due to excessive molecular weight from affecting the subsequent reaction, and thus is more conducive to the subsequent reaction. The polydispersity index decreases after reduction. The above results indicate that the C—I bond on the fluorine-containing alternating copolymer has been reduced, and macromonomer synthesis can be carried out in the next step.

Example 3 Synthesis of Fluorine-Containing Alternating Copolymer Macromonomer (1) Addition with Mercaptoethanol:
1,1'-azobis(cyanocyclohexane) (ABCN) was used as a catalyst to initiate the addition of the reduced fluorine-containing alternating copolymer $(AB)_n$ with β-mercaptoethanol. A fluorine-containing alternating polyolefin having a terminal hydroxyl group (—OH) was obtained, and then the terminal hydroxyl group was reacted with methacryloyl chloride to finally produce a fluorine-containing alternating copolymer macromonomer. The reaction route and steps were as follows.

The reduced fluorine-containing alternating copolymer (1 eq.) prepared in Example 2, ABCN (3 eq.), toluene (4.0 mL), and β-mercaptoethanol (20 eq.) were weighed in proportion sequentially and added to a 5 mL ampoule. After adding a stir bar, three rounds of freezing-evacuating-introducing argon were performed, and the ampoule was flame-sealed. The ampoule was placed in an oil bath at 90° C., stirred, reacted for a predetermined period of time and then removed. The ampoule was opened, and the solution was diluted with 1-2 mL of tetrahydrofuran, precipitated in a large amount of methanol in a disposable plastic cup, sealed with a plastic wrap and allowed to stand overnight in a refrigerator. Suction filtration under reduced pressure afforded a white product. The resulting white product was dried to a constant weight in a thermostatic oven at 40° C. under vacuum, and then weighed. Finally, a hydroxyl-terminated fluorine-containing alternating copolymer was obtained.

Figure 5:
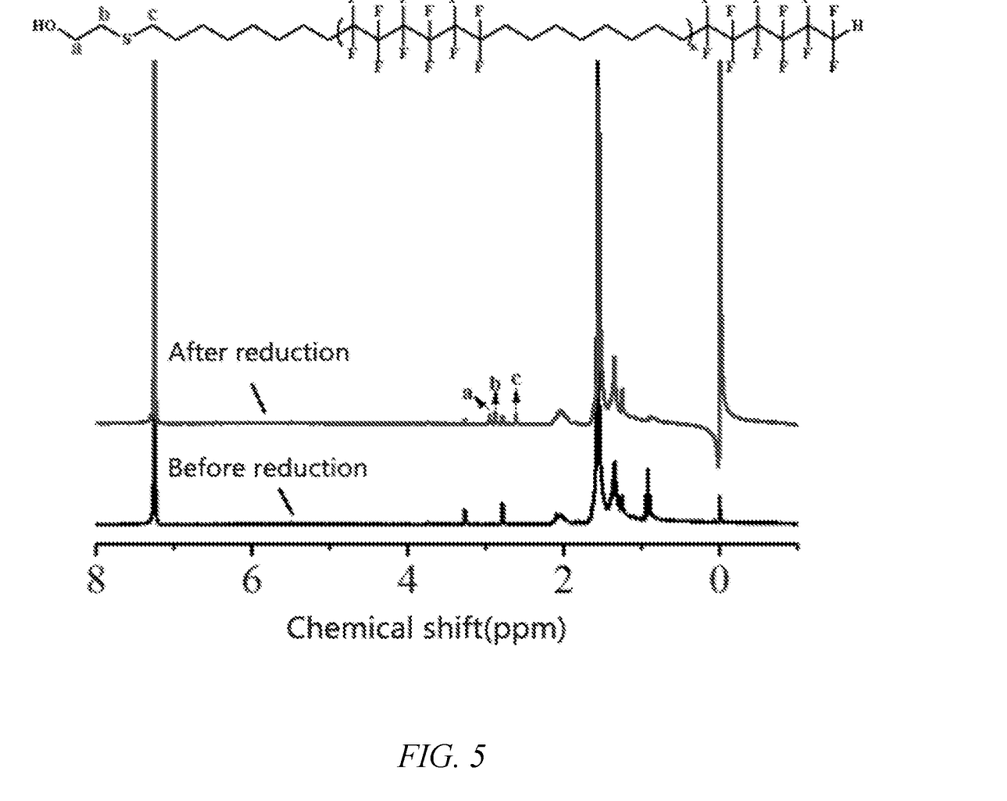
FIG. 5 shows the test results by $^1$H NMR of a reduced fluorine-containing alternating copolymer before and after reaction with mercaptoethanol in Example 3 of the present invention.

FIG. 5 shows the test results by $^1$H NMR of a reduced fluorine-containing alternating copolymer before and after reaction with mercaptoethanol. The peaks indicated by letters on the $^1$H NMR spectrum are attributed to the hydrogen atoms indicated by the same letters in the corresponding structural formula. It can be seen from the figure that the reaction is completed successfully. Two new shift peaks of mercaptoethanol are generated on the $^1$H NMR spectrum, and the double bond peak disappears completely. When not reduced, due to the higher C—I bond activity and lower bond energy, it can react with thiol to form HI, which inhibits the addition reaction of double bond with thiol. After reduction of the C—I bond, the free radical addition reaction occurs as expected, and it can be confirmed from the $^1$H NMR spectrum of FIG. 5 that a hydroxyl-terminated fluorine-containing alternating copolymer is synthesized.

(2) Reaction with Methacryloyl Chloride

The hydroxyl-terminated fluorine-containing alternating copolymer (1 eq.) obtained in Step (1), chloroform (3 mL), triethylamine (1.5 eq.), and methacryloyl chloride (1.5 eq.) were weighed in proportion sequentially and added to a 5 mL ampoule. After adding a stir bar, three rounds of freezing-evacuating-introducing argon were performed, and the ampoule was flame-sealed. The ampoule was placed in a water bath at 25° C., stirred, reacted for a predetermined period of time and then removed. The solution was diluted with 1-2 mL of tetrahydrofuran, precipitated in a large amount of methanol in a disposable plastic cup, sealed with a plastic wrap and allowed to stand overnight in a refrigerator. Suction filtration under reduced pressure afforded a white product. The resulting white product was dried to a constant weight in a thermostatic oven at 40° C. under vacuum, and then weighed. Finally, a fluorine-containing alternating copolymer macromonomer was obtained.

Figure 6:
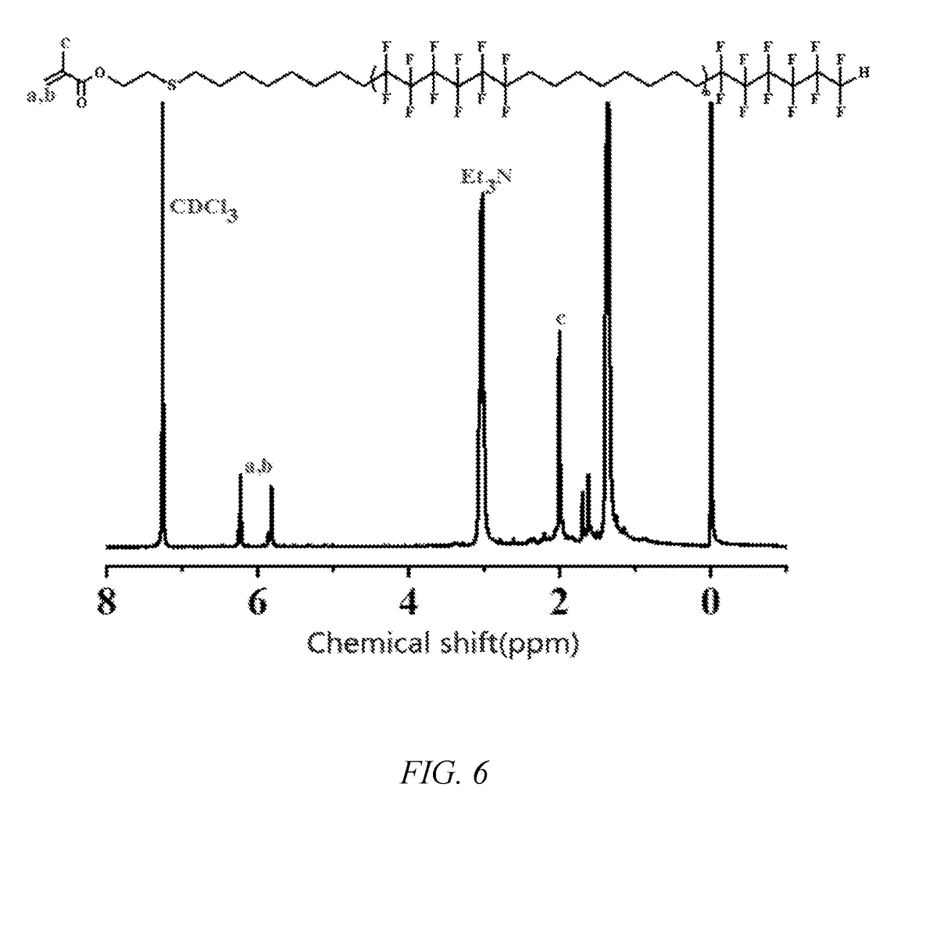
FIG. 6 shows the test results by $^1$H NMR of a macromonomer produced by reacting a hydroxyl-terminated fluorine-containing alternating copolymer with methacryloyl chloride in Example 3 of the present invention.

The $^1$H NMR spectrum of the macromonomer produced by the reaction of the hydroxyl-terminated fluorine-containing alternating copolymer with methacryloyl chloride is shown in FIG. 6. The peaks at different chemical shifts on the $^1$H NMR spectrum can be attributed to corresponding moieties in the structural formula. The shift peak at about 3 ppm is the shift peak of the catalyst triethylamine (Et$_3$N), and the peak at 7.26 ppm is the shift peak of the solvent deuterated chloroform (CDCl$_3$). The results show that the fluorinated alternating copolymer macromonomer is successfully obtained through the above method.

Comparative Examples

Figure 7:
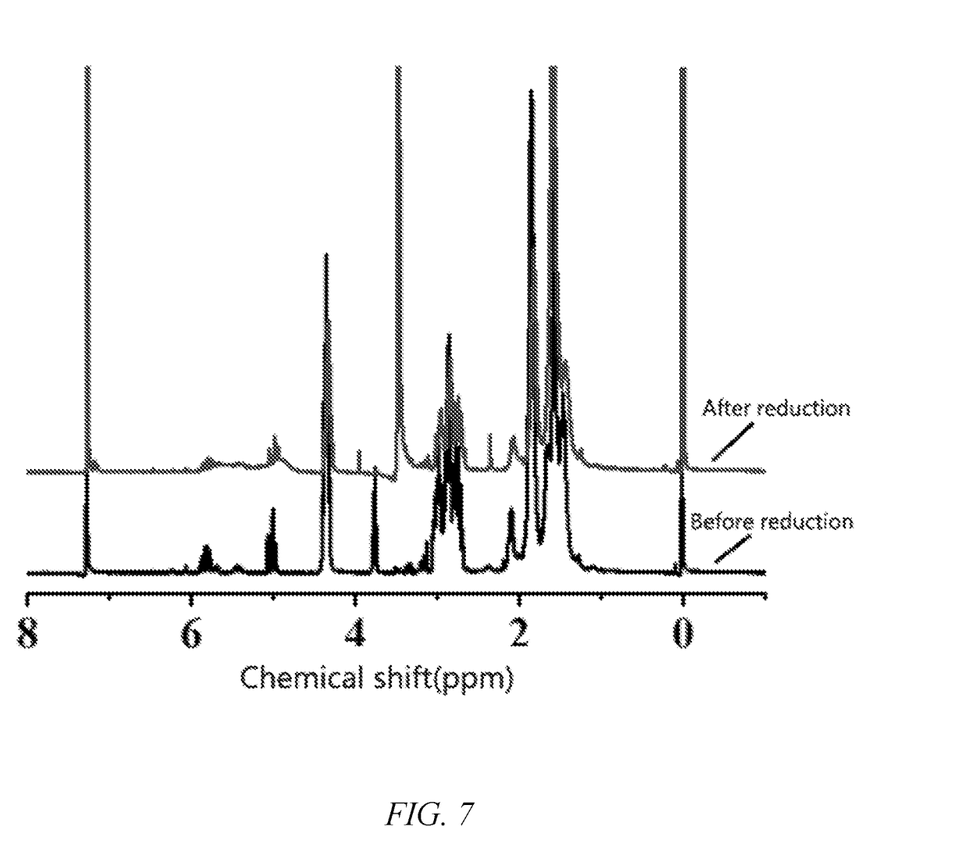
FIG. 7 shows the test results by $^1$H NMR of the product obtained by directly reacting of a non-reduced fluorine-containing alternating copolymer $(AB)_n$ with mercaptoethanol in the comparative example.

After the fluorine-containing alternating copolymer (AB)$_n$ in Example 1 was obtained, it was directly subjected to an addition reaction with mercaptoethanol (as shown in Table 1: the molar ratio of the fed materials, the reaction time, the catalyst type, the solvent type and volume, and others were varied). Theoretically, the terminal double bond of the fluorine-containing alternating copolymer reacts with thiol. However, the analysis of $^1$H NMR spectra (FIG. 7) shows that the peak shape and number of the double bond are basically unchanged (where only the solvent peak is changed, where after modification with mercaptoethanol, the shift peak of —CH$_2$ in tetrahydrofuran (THF) at 3.76 ppm disappears, and the shift peak of —CH$_3$ in methanol appears at 3.49 ppm). It can also be seen from the results by GPC that the molecular weight of the polymer basically remains the same.

TABLE 1

Reaction of fluorine-containing alternating copolymer (AB)$_n$ with mercaptoethanol under different conditions

| Comparative Examples | [(AB)$_n$]$_0$: [Bu$_3$HSn]$_0$: [initiator]$_0$ | Time (h) | Solvent | V$_{Solvent}$ (mL) | $^a$M$_n$ (g/mol) | $^a$PDI | $^b$M$_n$ (g/mol) | $^b$PDI |
|---|---|---|---|---|---|---|---|---|
| 1 | 1:10:0.5 | 10 | Toluene | 4 | 6600 | 1.47 | 7700 | 1.62 |
| 2 | 1:10:0.5 | 24 | Toluene | 4 | 6700 | 1.57 | 6500 | 1.55 |
| 3 | 1:10:0.5 | 48 | Toluene | 4 | 5000 | 1.39 | 4600 | 1.50 |
| 4 | 1:20 AM:1 | 24 | Toluene | 4 | 5900 | 1.56 | 5900 | 1.55 |
| 5 | 1:100:5 | 48 | Toluene | 4 | 5900 | 1.56 | 6200 | 1.52 |
| 6 | 1:20 AM:3 | 24 | Toluene | 4 | 5900 | 1.56 | 6000 | 1.33 |
| 7 | 1:20 AM:3 | 24 | Toluene | 2 | 8800 | 1.50 | 9200 | 1.43 |
| 8 | 1:40 AM:6 | 24 | Toluene | 2 | 8800 | 1.50 | 9300 | 1.40 |
| 9 | 1:20 AM:3 | 48 | Toluene | 2 | 8800 | 1.50 | 9300 | 1.48 |
| 10 | 1:20 AM:3 | 24 | DMSO | 2 | 8800 | 1.50 | 12300 | 1.37 |
| 11 | 1:20 AM:3 | 24 | DMF | 2 | 8800 | 1.50 | 11300 | 1.42 |

In Comparative Examples 1-5, the initiator is AIBN, and in Comparative Examples 6-11, the initiator is ABCN. $^a$M$_n$ is the molecular weight of (AB)$_n$ before reaction with mercaptoethanol, and $^a$PDI is the polydispersity index of (AB)$_n$ before reaction with mercaptoethanol. $^b$M$_n$ is the molecular weight of (AB)$_n$ after reaction with mercaptoethanol, and $^b$PDI is the polydispersity index of (AB)$_n$ after reaction with mercaptoethanol.

While preferred embodiments of the present invention have been described above, the present invention is not limited thereto. It should be appreciated that some improvements and variations can be made by those skilled in the art without departing from the technical principles of the present invention, which are also contemplated to be within the scope of the present invention.

What is claimed is:

1. A method for synthesizing a fluorine-containing alternating copolymer macromonomer, comprising steps of:
   (1) subjecting a fluorine-containing alternating copolymer of Formula (1) to a reduction reaction at 60-100° C. in an organic solvent in the presence of a reducing agent and a first catalyst, to obtain a reduction product of Formula (2) after the reaction is completed:

where a=4-8, b=2-6, and n=1-30;
   (2) in the presence of a second catalyst, reacting the reduction product with a mercapto-monohydric alcohol of Formula (3) in an organic solvent at 60-100° C., to obtain a hydroxyl-terminated fluorine-containing alternating copolymer of Formula (4) after the reaction is completed:

where c=1-10, a=4-8, b=2-6, and n=1-30; and
   (3) in the presence of a third catalyst, reacting the hydroxyl-terminated fluorine-containing alternating copolymer with an acrylic monomer or acryloyl chloride monomer at 0-30° C., to obtain the fluorine-containing alternating copolymer macromonomer after the reaction is completed.

2. The synthesis method according to claim 1, wherein in Step (1), the molar ratio of the fluorine-containing alternating copolymer and the reducing agent is 1:2-100, and the reducing agent is tributyltin hydride.

3. The synthesis method according to claim 1, wherein in Step (1), the molar ratio of the fluorine-containing alternating copolymer and the first catalyst is 1:2-300, and the first catalyst is azobisisobutyronitrile, or dibenzoyl peroxide.

4. The synthesis method according to claim 1, wherein in Step (2), the second catalyst is 1,1'-azo (cyanocyclohexane), or azobisisobutyronitrile; and the molar ratio of the reduction product and the second catalyst is 1:3-6.

5. The synthesis method according to claim 1, wherein in Step (2), the molar ratio of the reduction product to the mercapto-monohydric alcohol is 1:10-100.

6. The synthesis method according to claim 1, wherein in Step (3), the third catalyst is triethylamine or pyridine; and the molar ratio of the hydroxyl-terminated fluorine-containing alternating copolymer to the third catalyst is 1:1.5-2.

7. The synthesis method according to claim 1, wherein in Step (3), the acrylic monomer is methacrylic acid or acrylic acid.

8. The synthesis method according to claim 1, wherein in Step (3), the acryloyl chloride monomer is methacryloyl chloride, or acryloyl chloride.

9. The synthesis method according to claim 1, wherein in Step (3), the molar ratio of the hydroxyl-terminated fluorine-containing alternating copolymer to the acrylic monomer or acryloyl chloride monomer is 1:1.1-2.

10. A fluorine-containing alternating copolymer macromonomer prepared by the method according to claim 1, having a chemical Formula (5):

where R=H or $CH_3$, c=1-10, a=4-8, b=2-6, and n=1-30; and the fluorine-containing alternating copolymer macromonomer has a molecular weight of 540-16500 g/mol.

* * * * *